Figure 1:
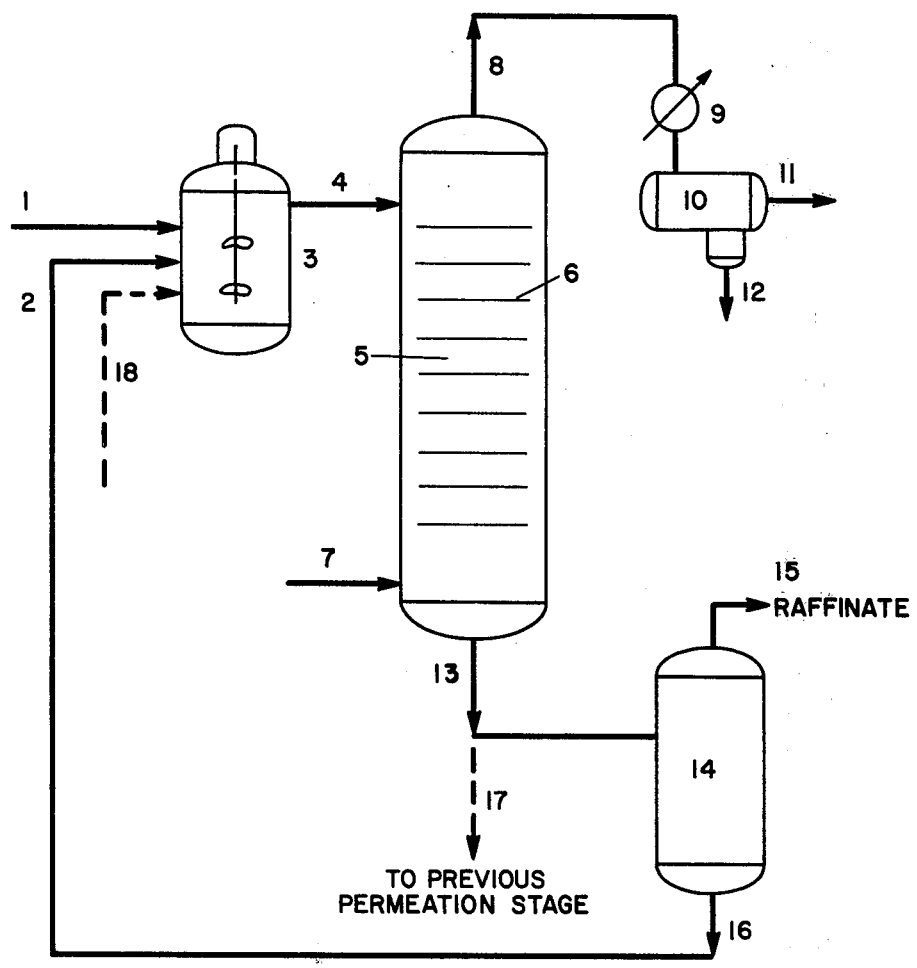

United States Patent [19]

Li et al.

[11] 4,155,844
[45] * May 22, 1979

[54] SEPARATION PROCESS

[75] Inventors: Norman N. Li, Edison; Robert P. Cahn, Millburn, both of N.J.

[73] Assignee: Exxon Research & Engineering Co., Florham Park, N.J.

[ * ] Notice: The portion of the term of this patent subsequent to Nov. 1, 1994, has been disclaimed.

[21] Appl. No.: 845,854

[22] Filed: Oct. 27, 1977

Related U.S. Application Data

[62] Division of Ser. No. 382,468, Jul. 25, 1973, Pat. No. 4,056,462.

[51] Int. Cl.² .............................................. B01D 13/00
[52] U.S. Cl. ................................. 210/22 R; 210/23 R
[58] Field of Search ............... 208/308, 177, 263, 311; 210/23 R, 22 R; 260/674 R

[56] References Cited

U.S. PATENT DOCUMENTS

| | | | |
|---|---|---|---|
| 3,650,091 | 3/1972 | Li ............................................ | 55/83 |
| 3,696,028 | 10/1972 | Li et al. ................................. | 208/308 |
| 4,056,462 | 11/1977 | Li et al. ................................. | 208/308 |

*Primary Examiner*—Herbert Levine
*Attorney, Agent, or Firm*—Ernest A. Forzano; David W. Collins

[57] ABSTRACT

The instant invention relates to a process for separating components from liquid mixtures which comprises emulsifying said liquid mixture in an immiscible liquid which is characterized as a solvent for the components. The emulsion is then contacted with an inert gas whereby the components of the mixture which, because of their solubility, permeate into said immiscible liquid, and are stripped therefrom by the inert gas. The components may then be separated from said inert gas stream by condensation and subsequent phase separation or fractionation, by absorption, distillation or by adsorption. In a preferred embodiment of the instant invention the liquid mixture comprises a hydrocarbon which is emulsified in an aqueous surfactant containing liquid. The hydrocarbon mixture contains hydrocarbons of different types, as well as hydrocarbons mixed with oxygenated compounds, i.e. alcohols, ketones, acids, and mixtures thereof. In a particular embodiment the hydrocarbon mixture contains toluene and heptane. In this embodiment the toluene preferentially permeates into said aqueous surfactant containing liquid and is removed therefrom by a stream of stripping steam.

6 Claims, 1 Drawing Figure

SINGLE STAGE OF SEPARATION PROCESS

SINGLE STAGE OF SEPARATION PROCESS

SEPARATION PROCESS

This is a division of application Ser. No. 382,468, filed July 25, 1973, now U.S. Pat. No. 4,056,462.

FIELD OF THE INVENTION

Background of the Prior Art

Processes for separating hydrocarbons by use of liquid membrane permeation are known in the art. See, for example, U.S. Pat. No. 3,410,794. In the process disclosed in this patent, a hydrocarbon mixture is emulsified thereby forming a liquid membrane around the emulsified hydrocarbon droplets. The emulsion is then contacted with a solvent which is immiscible with the external phase of the hydrocarbon emulsion; that is, the hydrocarbon emulsion is dispersed in a solvent which is immiscible with said aqueous surfactant containing solution. Components of the hydrocarbon mixture, depending on their solubility in the aqueous surfactant liquid, permeate through said aqueous surfactant into said solvent. The solvent and the emulsion are contacted under mild agitation conditions and the emulsion depleted in the more permeable component is recovered by discontinuing the agitation and separating the solvent from the emulsion phase. This patented process differs from the process of the instant invention in that it is nowhere contemplated that an inert gas, i.e. steam, nitrogen, etc., may be substituted for the solvent phase of the patented process.

In U.S. Pat. No. 3,650,091, a process for the separation of gaseous mixtures is claimed which comprises forming a foam of said gaseous mixture by passing said gaseous mixture through a surfactant containing solution. The foam may be characterized as liquid membrane encapsulated gas bubbles. The various components of the gaseous mixture permeate through said liquid membrane at varying rates dependent on the relative solubility of the individual components in the surfactant solution. A gaseous mixture enriched in the more permeable component is collected on the outside of the liquid membrane encapsulated gas bubbles and removed therefrom by use of a sweep gas. The patented process differs from the instant invention in that the patentee discloses only the separation of gaseous mixtures and the transfer of the separated components into a gas stream.

SUMMARY OF THE INVENTION

The instant invention relates to a process for separating components from liquid mixtures which comprises emulsifying said liquid mixture in an immiscible liquid which is characterized as a solvent for said components. The resulting emulsion is contacted with an inert gas whereby the components which, because of their solubility, permeate from the liquid mixture into the immiscible liquid, are removed therefrom by stripping with the inert gas.

The instant invention is particularly related to a separation of mixtures containing hydrocarbons by emulsifying said mixture in an aqueous surfactant containing solution. This solution is then contacted with an inert gas thereby removing the components of the mixture, which have permeated into the aqueous surfactant phase. Mixtures which may be separated include hydrocarbon mixtures containing close boiling components which are difficult to separate by conventional means, but differ in type, such as aromatics and paraffins, olefins or diolefins, and paraffins, ethylbenzene and styrene, aromatics and naphthenes. Other mixtures which can be separated are those containing a hydrocarbon and a functionalized hydrocarbon such as alcohols, ketones and aldehydes, acids, amines which are close boiling and therefore hard to separate by distillation.

In the subsequent description, all these mixtures will be referred to as hydrocarbon mixtures, although one of the constituents may indeed not be a hydrocarbon proper but an alcohol or amine, etc.

The hydrocarbon mixture to be separated is emulsified by mixing at a high shear rate with an aqueous surfactant containing solution. The surfactant may comprise from 0.01 to 90 weight percent of the aqueous solution, preferably from 0.01 to 5 weight percent. The surfactants may be chosen from the group consisting of ionic, cationic and nonionic surfactants. Examples of surfactants which may be conveniently used include the water soluble salts of long chain carboxylic acids, e.g., those containing from 12 to 18 carbon atoms per molecule; aliphatic sulfonates, and alkyl aromatic sulfonates, for example, sodium tetradecanesulfonate, alkylated naphthalene sulfonate, alkylated benzene sulfonate, etc., in general comprising from 10 to 30 carbon atoms per surfactant molecule; aliphatic sulfates, i.e., those surfactants formed by esterifying fatty alcohol with sulfuric acid; primary alpha amines, i.e. octadecyl amine, dodecyl amine, etc.; quaternary ammonium salts, wherein at least one alkyl group has from 8 to 20 carbon atoms; fatty esters of glycol, sorbitol and mannitol; fatty alcohol amides; and the ethylene oxide derivatives of alkylated phenols and fatty alcohols, etc. The surfactants which may be utilized in the instant invention are illimitable and it is not intended to burden this application with numerous examples.

The following publications are herein incorporated by reference; to disclose other surfactants which may be used in the practice of the instant invention:

*Surface Chemistry*, by Lloyd I. Osipo, Rheinhold Publishing Co., New York, 1962, Chapter 8

*Surface Activity*, Moilliet et al, Van Nostrand Co., 1961, Part 3.

The surfactant will be chosen with regard to the necessity of forming a stable emulsion in the instant process. The exterior phase of the emulsion functions as a membrane for the separation of the desired components from admixture, therefore, the importance of forming a stable emulsion may readily be seen. The exterior phase of the emulsion is also selected so as to allow solubility therein of the desired components of the liquid mixture. Thus, the choice of surfactant may be critical to the separation desired to be carried out; for example, when the hydrocarbon to be separated is an aromatic or other unsaturated hydrocarbon, anionic surfactants, because of their ability to promote the solubility of hydrocarbons of these types, are preferably used. Saponin is a particularly preferred surfactant for use in separating aromatics or polyolefins from less polar hydrocarbons by the process of the instant invention. In a preferred process for separating aromatics from a reforming feedstream, the feedstream may be conveniently emulsified in an aqueous 5% solution of saponin.

The components to be separated will permeate into the exterior phase of the emulsion leaving an interior phase depleted in this more permeable component. However, since an equilibrium distribution is involved, and in general the permeable component is even more soluble in the liquid mixture than in the exterior phase of the emulsion, only a small amount of permeable component will permeate into the exterior phase. For example, when separating a mixture of benzene and cyclohexane, the benzene is infinitely soluble in cyclohexane while water will only dissolve approximately 0.04–0.06 mol % benzene at 100°–160° F.

The addition of 5% of an anionic surfactant to the water will only increase the solubility of benzene slightly. The instant invention, however, provides a means for avoiding this problem of poor equilibrium distribution of the desired component between the exterior and interior phase of the emulsion.

In the instant invention an inert gas is passed through the emulsion to remove the more permeable component from the exterior phase. The inert gas may be the following, by themselves or admixed: steam, nitrogen, hydrogen, $CO_2$, a light, condensible hydrocarbon easily separated from the feed component, etc. As the gas is passed through the emulsion at a rate as determined by vapor pressure considerations at the operating temperature, the permeable component will be removed from the exterior phase and more of the permeable component present in the interior phase will permeate into the exterior phase of the emulsion, resulting in a selective depletion in the emulsion of the more permeable component. Thus, the ultimate separation will readily seem to depend on the solubility of the desired component in the exterior phase of the emulsion and the volatility of the desired component at the temperature and in the presence of the inert gas which is passed through the emulsion.

The exterior phase of the emulsion is designed to promote solubility of the desired components of the emulsified mixture therein. Thus, glycerol, and the like, which solubilizes aromatics and diolefins to a greater extent than water, may be conveniently used as a partial or total replacement in separating hydrocarbons of this type. The exterior phase of the emulsion is further designed to be stable at conditions of operation, thus glycerol and the other "membrane strengthening" additives described in U.S. Pat. No. 3,696,028 may be used in the process of the instant invention. Finally, when the instant process is operated at higher temperatures, e.g. >70° C., the exterior phase of the emulsion should be designed to be substantially nonvolatile at these conditions. Again, glycerol and other low vapor pressure water miscible solvents may be utilized in the instant process.

In a preferred embodiment of the instant invention the inert gas is steam. Steam is chosen because it is easily condensed and decanted from the constituents being separated. Also, water is one of the constituents of the membrane phase so that steam will be present in the vapor phase in any case.

The components which are removed from the liquid mixture by permeation into the exterior phase of the emulsion and stripping with an inert gas may be recovered by methods known in the art. For example, when the component is a hydrocarbon and the inert gas is steam, condensation of the mixture will provide a two-phase system with a hydrocarbon at the top and water at the bottom. The hydrocarbon may be conveniently removed from this two-phase mixture.

The process of the instant invention is carried out at a temperature and pressure which are sufficient to maintain the immiscible liquid and the liquid mixture in a liquid phase in order to maintain the emulsion is a stable condition. The emulsion breaking as discussed above of course, leads to nonselected stripping of the liquid mixture since the exterior phase of the emulsion no longer acts as a liquid membrane, permeable only to the desired components of the liquid mixture. Thus, breaking of the emulsion leads to decreased selectivity since, unless the liquid mixture is a discontinuous phase contained within a membrane formed by the continuous immiscible liquid phase, the permeability into the immiscible liquid does not provide selectivity.

In general, the process of the instant invention may be carried out at a temperature of from 5° C. to 150° C., preferably from 50° C. to 120° C. In the preferred process, wherein hydrocarbon mixtures are separated, the lowest temperature in which the process should be run should be higher than the freezing temperature of the aqueous surfactant solution and above the cloud point of any nonionic surfactants utilized to form the emulsion. The temperature should also be sufficiently higher than the freezing temperature of the solvent or hydrocarbon mixture to facilitate mass transfer. Also, since the partial pressure of the permeating component in the inert gas is a strong function of temperature, engineering considerations (achievable concentration) set a practical lower temperature limit to any particular separation. The pressure is conveniently atmospheric but may be increased or decreased in order to maintain all the components of the mixtures in a liquid phase. In the separation of hydrocarbons wherein said hydrocarbons are emulsified in an aqueous solution and stripped with steam, pressures of less than 1 atmosphere are conveniently utilized.

Since the exterior phase of the emulsion is an aqueous solution, it will exert a certain steam partial pressure at the process temperature, as determined by the vapor pressure curve of this solution. Also, the hydrocarbon mixture will exert a given partial pressure which is a strict function of process temperature. Consequently, the emulsion effectively will exert a vapor pressure somewhat less than the sum of these two partial pressures, so that process temperature and pressure are obviously not independent variables.

It is generally desirable to operate at the maximum temperature commensurate with a stable membrane formulation and under conditions where the internal phase does not actively boil, as this would rupture the membrane. Of course, it is also mandatory that the exterior, i.e. aqueous phase, not be actively boiling, although it must be, by virtue of the above vapor pressure considerations, at its boiling point when steam is present as the vapor.

Operating temperatures with steam as inert gas will generally range between 50° C. and 150° C., but usually not over 120° C. Pressure generally will be between 2–100 psia. With a very light internal phase, say a mixture of $C_3$ hydrocarbons, pressures in excess of 200 psia may be required to restrain the internal phase from boiling. However, with constituents in the $C_5$–$C_{10}$ range, pressures ranging from 2–100 psia are generally adequate.

The maximum temperature is, of course, also limited by the thermal stability of the constituents of the system, in particular the surfactant employed. Also, many surfactants have operating temperature ranges and lose their surfactancy when this range is exceeded.

In a particular embodiment of this invention, a mixture of toluene and heptane can be separated by emulsifying the hydrocarbon mixture in an aqueous glycerine solution containing saponin as a surfactant and stripping the emulsion with an inert gas such as steam. The separation is preferably carried out in a multistage column, and the permeate, i.e. the hydrocarbon which has permeated from the feed mixture out through the exterior aqueous phase and has been stripped into the vapor phase, can be recovered by condensation of the overhead, followed by phase separation of the water and hydrocarbon layers.

The invention can be best understood by reference to the attached drawing, FIG. 1, which represents a single stage in a possible cascade of repeated permeation stages.

The hydrocarbon feed mixture comprising heptane and toluene is fed via line 1 into emulsifier vessel 3 where it is mixed with the aqueous phase introduced via line 2. The aqueous phase comprises a solution containing 30% water, 69% glycerine and 1% saponin. In emulsifier 3 the hydrocarbon mixture is emulsified in small droplets in the aqueous solution which is the external phase. More than one vessel 3 may be employed to work in series, or to operate alternatively in batch in a staggered operation.

The finished emulsion, which may also include some emulsion which has been recycled from a subsequent cascade stage, is now fed via line 4 into permeator tower 5 which is provided with vapor-liquid contacting trays 6. A packed tower can also be used. In tower 5, the emulsion is contacted in a countercurrent manner with stripping steam, introduced at the bottom of the column via line 7. As the emulsion descends from tray to tray, the toluene will permeate more rapidly than the heptane from the hydrocarbon droplets through the exterior aqueous membrane phase into the stripping steam rising through the column, and will be removed as overhead vapor through line 8, condensed in exchanger 9 and allowed to settle in drum 10. The hydrocarbon layer, much enriched in toluene relative to the feed composition, is withdrawn by line 11, and may be fed to a subsequent stage in the cascade. The steam condensate is withdrawn via draw-off 12. If a light hydrocarbon had been used in place of steam, a distillation column or flash device would have been substituted for condenser 9 and settling drum 10. If a permanent gas, i.e. nitrogen or hydrogen, is used in place of steam, the phase separation in drum 10 would be between a liquid (permeate) phase and a vapor phase (stripping gas plus equilibrium quantity of permeate vapor).

The column bottoms liquid, taken off via line 13, is the raffinate emulsion, enriched in heptane relative to toluene when compared to the feed mixture. It may be sent to demulsification zone 14, where the hydrocarbon phase is separated from the aqueous phase by a number of means such as settling, centrifugation, distillation, or other physical means of separation. The hydrocarbon raffinate may be taken off as a product or passed back to a previous permeation stage in the separation cascade. The aqueous phase may of course be recycled via line 16 to the emulsifier 3 or any other emulsifier. Alternatively, the unseparated raffinate emulsion as a whole may be fed via line 17 back into the previous permeation cascade stage, preferably into the emulsifier of that cascade, corresponding to vessel 3 of the instant stage. Such a recycle is shown by line 18 in the instant cascade stage.

If we define the degree of separation, S, achieved with a feed mixture of constituents A and B in a given process which splits the feed into a permeate (subscript P) and raffinate (subscript R) stream, then if we call the concentration of either A or B in P or R, $C_{AR}$, $C_{AP}$, $C_{BR}$ or $C_{BP}$, $$S = (C_{AP}/C_{BP}) \times (C_{BR}/C_{AR})$$

is a valuable expression to assess the effectiveness of a given separation scheme. For a single separation step, like on one plate, the degree of separation is often called the relative volatility, $\alpha$, in distillation.

For the system toluene-heptane the single step degree of separation for the system in the present invention may range from 4–20, depending on the conditions; for a multistage tower, this degree of separation may be several hundred, when comparing the compositions of raffinate 15 and permeate 11.

However, in actual practice, quite pure components are required as the product of a separation process, both for the purpose of attaining high purity product and good recovery. Consequently, an overall S of several thousand to 20–50,000 may be needed. This can be achieved in the present process by placing several of these separation stages in series, i.e. forming a processing cascade with countercurrent flow of permeate and raffinate from one stage in the cascade to the next.

Typical flow rates and compositions for a three-stage cascade separating a 50/50 toluene/heptane mixture into 99.8% toluene at 98% recovery is shown in attached Table 1.

From the above description it is apparent that a single stage can achieve separation of the 50/50 feed stock into a product, say, 80% pure aromatic and at 98% recovery, or, alternately, 90% pure and about 95% recovery. Consequently, the permeation process described in this application is particularly suitable to those cases where only partial separation is required, such as for the transfer of aromatic or olefin from one stream to another, or removal of a dilute reaction product from a large reactor recycle stream. Typical examples are the transfer of aromatics from a virgin naphtha or catalytic reformer feed to a high octane naphtha, or the removal of the olefin product of a catalytic dehydrogenation process from the reactor effluent to the purification section, allowing recycle of unconverted feed to the dehydrogenation zone. Another example is the removal of partially oxidized hydrocarbon in a low conversion per pass reaction, followed by work-up of the crude permeate in a final separation zone, including distillation and the like, but allowing the bulk of the unconverted hydrocarbon to by-pass the complex and expensive final separation zone.

The actual temperature and pressure in the permeation zone separating toluene and heptane in the above example were 2 psig and 210°–240° F. However, as discussed previously, the process can be operated at temperatures as low as 120° F. by dropping the pressure to 2 psia, while by raising the pressure to 50–75 psig or so, the temperature in the permeator can be allowed to go to 275°–300° F. Higher temperature leads to faster permeation rate, and, therefore, smaller equipment, but special emulsifier formulations have to be employed to assure emulsion stability at elevated temperatures.

EXAMPLE 1

This experiment demonstrates the idea that the exterior phase of an emulsion, functioning as a liquid membrane can be used to effect a desired separation. In this experiment a carrier gas is used to strip off the permeable component of the mixture. The carrier gas used is nitrogen. A mixture consisting of 57 g of 2,5-dimethylhexane (0.5 g mol) and 46 g of toluene (0.5 g mol) is emulsified in 100 g of an aqueous phase comprising 30% water, 69% glycerine and 1% saponin.

Nitrogen is passed through this emulsion at 100° F. and the effluent vapor analyzed for paraffin and aromatic. The ratio of the two constituents stripped from the emulsion during the initial period of operation is 15/1 aromatic/paraffin, dropping below this value as the operation continues due to the depletion of toluene in the emulsion.

When the same hydrocarbon mixture is stripped with nitrogen at 100° F. without prior emulsification in an aqueous phase, the amounts of hydrocarbon in the vapor are approximately in the ratio 1/1 aromatic paraffin.

EXAMPLE 2

The process of Example 1 is repeated, however the mixture contains 57 g of n-heptane and 46 g of toluene in place of the 2,5-dimethylhexane-toluene mixture of Example 1. When nitrogen is passed through the unemulsified mixture at 100° F. the hydrocarbon off-gas contains from about 30 to 50% by weight more heptane than toluene. The mixture is emulsified in the aqueous phase described in Example 1 and the emulsion stripped with nitrogen at 100° F. During the initial periods of the stripping operation the off-gas contains approximately ten times more toluene than heptane, thus demonstrating that toluene permeates much more rapidly into the exterior phase of the emulsion than heptane wherein it is removed by the inert gas stream.

What is claimed is:

1. Process for separating a functionalized hydrocarbon from a first liquid mixture containing functionalized hydrocarbons and hydrocarbons which comprises:
    (1) forming an emulsion of said mixture in an aqueous surfactant solution, said emulsion comprising a discontinuous hydrocarbon phase and a continuous aqueous surfactant solution phase;
    (2) passing a portion being enriched in functionalized hydrocarbons into said aqueous surfactant solution;
    (3) passing steam through said emulsion at conditions whereby said liquid mixture is restrained from boiling to remove a mixture of functionalized hydrocarbons, hydrocarbons and steam, said removed mixture being enriched in functionalized hydrocarbons;
    (4) condensing said removed mixture to separate steam from said removed mixture whereby a second mixture containing functionalized hydrocarbons and hydrocarbons is formed and said second mixture is enriched in functionalized hydrocarbons;
    (5) returning said second mixture to an emulsion zone; and
    (6) repeating steps (1), (2), (3) and (4) until the desired content of functionalized hydrocarbons is obtained.

2. The process of claim 1 wherein said aqueous surfactant solution comprises glycerine.

3. The process of claim 2 wherein said first mixture comprises oxygenated hydrocarbons and hydrocarbons.

4. The process of claim 3 wherein said aqueous surfactant containing solution comprises from 0.1 to 10% surfactant.

5. The process of claim 4 wherein said surfactant is saponin.

6. The process of claim 1 wherein said functionalized hydrocarbon is selected from the group consisting of alcohols, ketones, aldehydes, acids and amines.

* * * * *